United States Patent [19]
Deckman et al.

[11] Patent Number: 5,984,867
[45] Date of Patent: Nov. 16, 1999

[54] SURGICAL RETRACTOR AND METHOD OF RETRACTING

[75] Inventors: Robert K. Deckman, San Mateo, Calif.; Jeffrey W. Krier, Port Orchard, Wash.; Scott H. Miller, Sunnyvale, Calif.

[73] Assignee: Heartport, Inc., Redwood City, Calif.

[21] Appl. No.: 08/911,877

[22] Filed: Aug. 15, 1997

Related U.S. Application Data
[60] Provisional application No. 60/045,296, May 2, 1997.

[51] Int. Cl.$^6$ .................................................. A61B 17/02
[52] U.S. Cl. ........................................... 600/232; 600/231
[58] Field of Search .................................... 600/201, 227, 600/231, 232, 233, 234, 210, 213, 217; 128/898

[56] References Cited

U.S. PATENT DOCUMENTS

| | | |
|---|---|---|
| Re. 34,150 | 12/1992 | Santilli et al. . |
| 2,642,862 | 6/1953 | Jackson ............................... 600/234 X |
| 3,384,078 | 5/1968 | Gauthier . |
| 3,572,326 | 3/1971 | Jensen . |
| 3,710,783 | 1/1973 | Jascalevich . |
| 3,724,449 | 4/1973 | Gauthier . |
| 3,782,370 | 1/1974 | McDonald . |
| 3,807,393 | 4/1974 | McDonald . |
| 3,863,639 | 2/1975 | Kleaveland . |
| 4,151,838 | 5/1979 | Crew . |
| 4,344,420 | 8/1982 | Forder . |
| 4,355,631 | 10/1982 | LeVahn . |
| 4,457,300 | 7/1984 | Budde . |
| 4,622,955 | 11/1986 | Fakhrai . |
| 4,627,421 | 12/1986 | Symbas et al. . |
| 4,702,230 | 10/1987 | Pelta . |
| 4,726,356 | 2/1988 | Santilli et al. . |
| 4,747,395 | 5/1988 | Brief . |
| 4,813,401 | 3/1989 | Grieshaber . |

(List continued on next page.)

FOREIGN PATENT DOCUMENTS

| | | |
|---|---|---|
| 0769269 | 4/1997 | European Pat. Off. . |
| 0792620 | 9/1997 | European Pat. Off. . |
| 3834358 | 12/1990 | Germany . |
| 4028651 | 3/1992 | Germany . |
| 2267827 | 12/1993 | United Kingdom . |

OTHER PUBLICATIONS

Ancalmo and Ochsner, "A Modified Sternal Retractor," *Ann Thorac Surg*, 1976;21(2):174.
Beg et al., "Internal Mammary Retractor," *Ann Thorac Surg*, 1985;39(3):286–287.
Cardio Thoracic Systems, Inc. Press Release, "Cardio Thoracic Systems Introduces Next Generation Beating Heart System" Yahoo/PR Newswire, 1997, 2 pages.

(List continued on next page.)

*Primary Examiner*—Jeffrey A. Smith
*Attorney, Agent, or Firm*—Jeffry J. Grainger; Jens E. Hoekendijk

[57] ABSTRACT

A surgical retractor has a frame and first and second retractor blades coupled to the frame. The retractor blades engage opposite sides of an incision in a patient's body and are relatively movable toward or away from each other along a first axis. When using the retractor in lift mode, a foot is coupled to the frame or one of the blades and engages the patient's body adjacent the incision. An actuator imparts relative movement to the retractor blades along the first axis and the foot acts as a support base with one of the blades moving relative to the frame to lift the ribs at one side of the incision above the other. To use the retractor in spread mode the foot is removed and the retractor blades spread of the ribs without lifting. The retractor may be used in various modes to facilitate a variety of surgical procedures, including, for example, harvesting the right or left internal mammary artery, repair or replacement of the mitral and aortic valves, proximal anastamosis of arterial conduits to the aorta, distal anastamosis of the conduits to coronary arteries, and any of various other procedures requiring access to the heart, great vessels, lungs, or other thoracic contents.

12 Claims, 10 Drawing Sheets

U.S. PATENT DOCUMENTS

| | | |
|---|---|---|
| 4,829,985 | 5/1989 | Couetil . |
| 4,852,552 | 8/1989 | Chaux . |
| 4,865,019 | 9/1989 | Phillips . |
| 4,884,559 | 12/1989 | Collins . |
| 4,949,707 | 8/1990 | LeVahn et al. . |
| 4,989,587 | 2/1991 | Farley . |
| 5,025,779 | 6/1991 | Bugge .................................. 600/232 X |
| 5,027,793 | 7/1991 | Engelhardt et al. . |
| 5,074,858 | 12/1991 | Ramos Martinez . |
| 5,088,472 | 2/1992 | Fakhrai . |
| 5,125,396 | 6/1992 | Ray . |
| 5,167,223 | 12/1992 | Koros et al. . |
| 5,365,921 | 11/1994 | Bookwalter et al. . |
| 5,730,757 | 3/1998 | Benetti et al. . |

OTHER PUBLICATIONS

Cardio Thoracic Systems, Inc. product advertisement/brochure for CTS MIDCAB, LIMA–lift, LIMA–Loop P/N 00095 Rev A, no date.

Cardio Thoracic Systems, Inc. product advertisement/brochure for CTS MIDCAB Access Platform and Stabilizer P/N 00050 Rev A, no date.

Cardio Thoracic Systems, Inc. product advertisement for CTS MIDCAB Access Platform and Stabilizer, no date.

Chaux and Blanche, "A New Concept in Sternal Retraction: Applications for Internal Mammary Artery Dissection and Valve Replacement Surgery," *Ann Thorac Surg*, 1986;42:473–474.

Kapp Surgical Instrument Inc. Minimally Invasive Kapp–Zapolanski Retracor product advertisement/brochure, no date.

Kapp Surgical Instrument Inc., Multi–Purpose Mid–Cab Retractor product advertisement/brochure, no date.

McKeown et al., "A Modified Sternal Retractor for Exposure of the Internal Mammary Artery," *Ann Thorac Surg*, 1981;32(6):619.

Omni–Tract Surgical Mini Retractor Systems product advertisement/brochure, 1996.

Omni–Tract Surgical Surgical Retraction Systems, 1996.

Omni–Tract Surgical product advertisement/brochure for The System and Reusable, Non–Endo DirectVision CAB, 1997. 40–6099.

Rultract, Inc. IMA Retractor product brochure, 1991.

Rultract Incorporated Surgical Retractor Systems product advertisement/brochure, no date.

Scanlan CardioVasive instrumentation product advertisement/brochure, 1997.

St. Jude Medical, Inc. Rosenkranz Pediatric Open Heart Retractor product advertisement/brochure, 1993.

Snowden–Pencer product brochure/advertisement for Endo–CABG Rib Spreader/Retractor, no date.

USSC Cardiovascular Marketing Newsletter, 1996;I(1):1–4.

Chapter 26, Surgical Procedures to Resect and Replace the Esophagus, p. 13, no date.

"A Retractor for Cholecystectomy", The Lancet, New Inventions, p. 854, Oct. 1955.

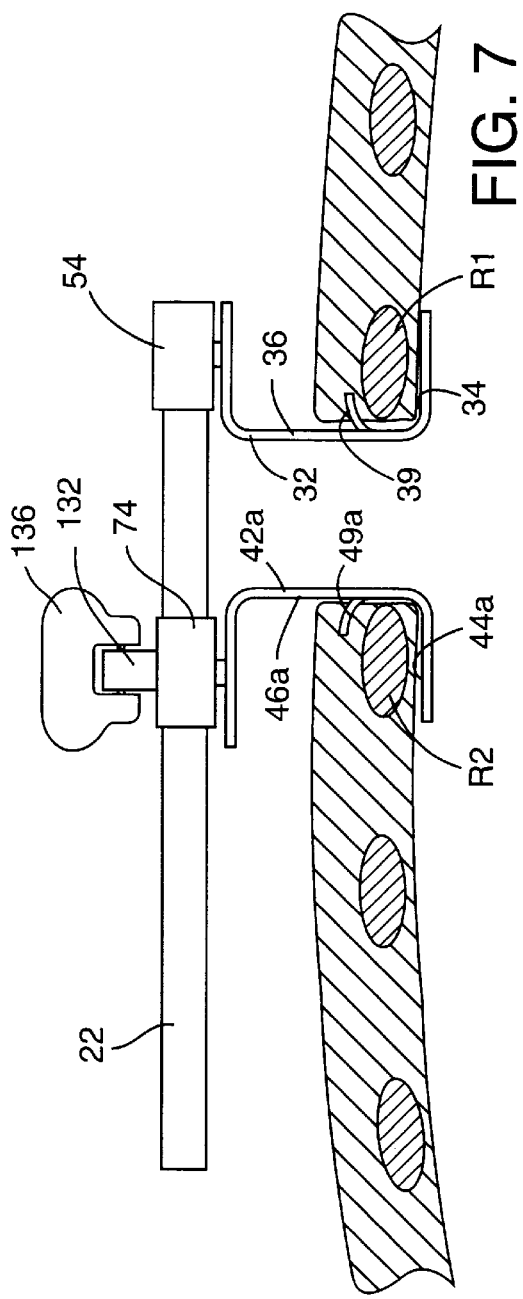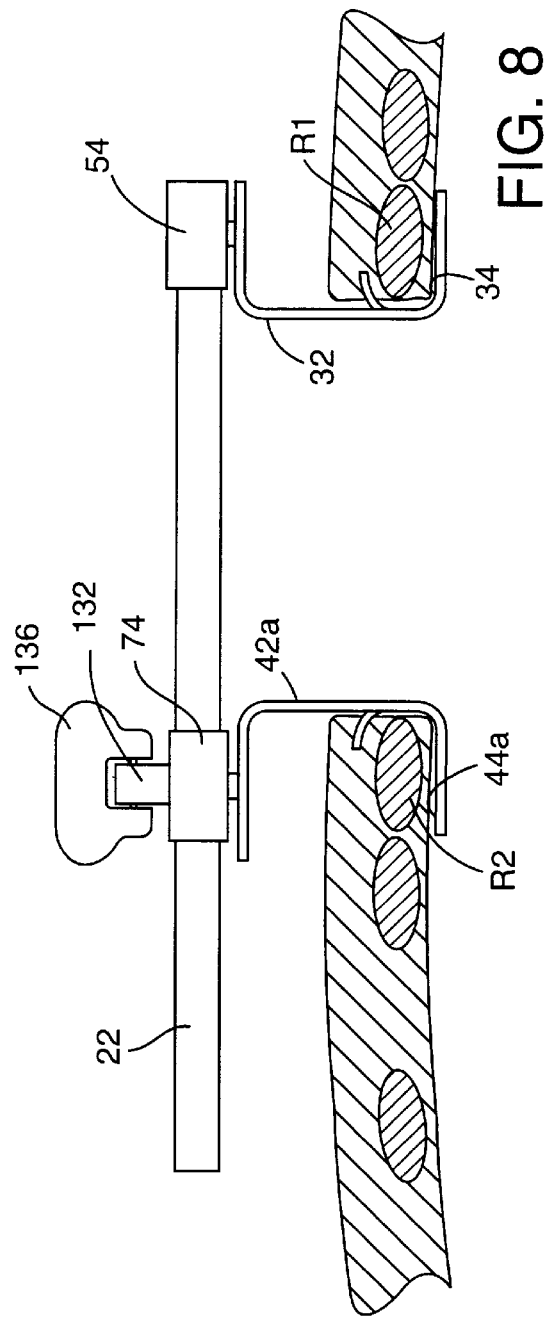

SURGICAL RETRACTOR AND METHOD OF RETRACTING

This application claims benefit of Provisional application Ser. No. 60/045,296 filed May 2, 1997.

BACKGROUND OF THE INVENTION

1. Field of the Invention

The present invention relates to retractors for use during surgery and, more particularly, for use in retracting ribs and adjacent tissue during surgery of the thorax.

2. Description of Related Art

During surgery it is frequently necessary to retract tissue, bone or other body material in order to facilitate access to and visualization of the surgical site. This is particularly true in surgery of the thorax. If access to the chest cavity is sought between the ribs, both the chest wall tissue and the ribs must be retracted to provide an opening large enough for insertion of surgical instruments and to allow visualization of the chest cavity, either directly through the incision or through an endoscope, microscope or other visualization device. In certain surgical procedures, such as coronary bypass grafting, it may be desirable to both lift the chest wall anteriorly and spread the ribs superiorly and inferiorly, for example, to harvest one or both of the internal mammary arteries located on the interior of the chest wall. During the same surgical procedure, it may be desirable, in addition to lifting and spreading the ribs, to only spread the ribs, depending upon the surgical manipulations to be performed.

Although many surgical retractor designs have been proposed, there remains a need in the art for a retractor that is able to perform various functions while having minimum size, few parts, and high ease of use.

SUMMARY OF THE INVENTION

A surgical retractor constructed according to the invention comprises a frame and first and second retractor blades coupled to the frame, the retractor blades having retraction surfaces configured to engage an incision in a patient's body. The first and second retractor blades are relatively movable toward or away from each other along a first axis to position the blades closer to or farther away from each other. A foot is coupled to the frame or one of the blades and has a support surface configured to engage a surface of the patient's body adjacent the incision. An actuator is provided for imparting relative movement to the retractor blades along the first axis. The foot acts as a support base and one of the blades moves relative to the frame to lift one side of the incision above the other, thereby facilitating a variety of surgical procedures, including, for example, accessing the underside of the chest wall to harvest the right or left internal mammary artery, repair or replacement of the mitral and aortic valves, proximal anastamosis of arterial conduits to the aorta and distal anastamosis of the conduits to coronary arteries, and any of various other procedures requiring access to the heart, great vessels, lungs, or other thoracic contents.

According to one specific preferred embodiment, at least one of the retractor blades is coupled to the frame so as to be rotatable with respect thereto about a second axis which is generally perpendicular to the first axis. The actuator moves the blades apart which, due to the foot acting a support base, causes the one blade to rotate with respect to the frame, such rotation occurring in a direction that lifts the side of the incision engaged by the rotating blade.

According to another specific embodiment, the foot preferably is movable with respect to the frame to permit adjustment of the relative position of the foot and the frame, such adjustment occurring along a third axis which is transverse, and preferably perpendicular to the first and second axes.

According to yet another specific embodiment, one of the retractor blades is rotatable about a second axis with respect to the frame and is coupled thereto so as to be movable between rotatable and non-rotatable positions. Locating the retractor blade in the non-rotatable position configures the retractor for spreading of the ribs (i.e., without lifting), while locating the blade in the rotatable position configures the retractor for lifting and spreading of the ribs.

A method of retracting a portion of a patient's body according to the invention comprises steps of positioning first and second retractor blades against opposite sides of an incision formed in a patient's body, the retractor blades being coupled to a frame so as to be relatively movable toward or away from each other along a first axis, and providing a foot configured to contact a surface of the patient's body adjacent the incision, the foot being coupled to the frame so as to be adjustable with respect thereto along a direction which is transverse to the first axis. The position of the foot is adjusted with respect to the frame to place the foot against the surface of the patient's body adjacent the incision, and relative movement is imparted to the first and second blades to simultaneously move the blades apart along the first axis and lift one side of the incision with respect to the other side of the incision.

Other features, benefits and advantages of the invention will become apparent from the following detailed description of preferred embodiments thereof, taken in conjunction with the accompanying drawing Figures.

BRIEF DESCRIPTION OF THE DRAWINGS

FIG. 7 is a sectional schematic view showing the retractor of FIG. 3 inserted into an incision formed in a patient's body;

FIG. 8 is a sectional schematic view showing the retractor of FIG. 7 being used to spread the opposite sides of the incision;

DETAILED DESCRIPTION OF PREFERRED EMBODIMENTS

Figure 1:
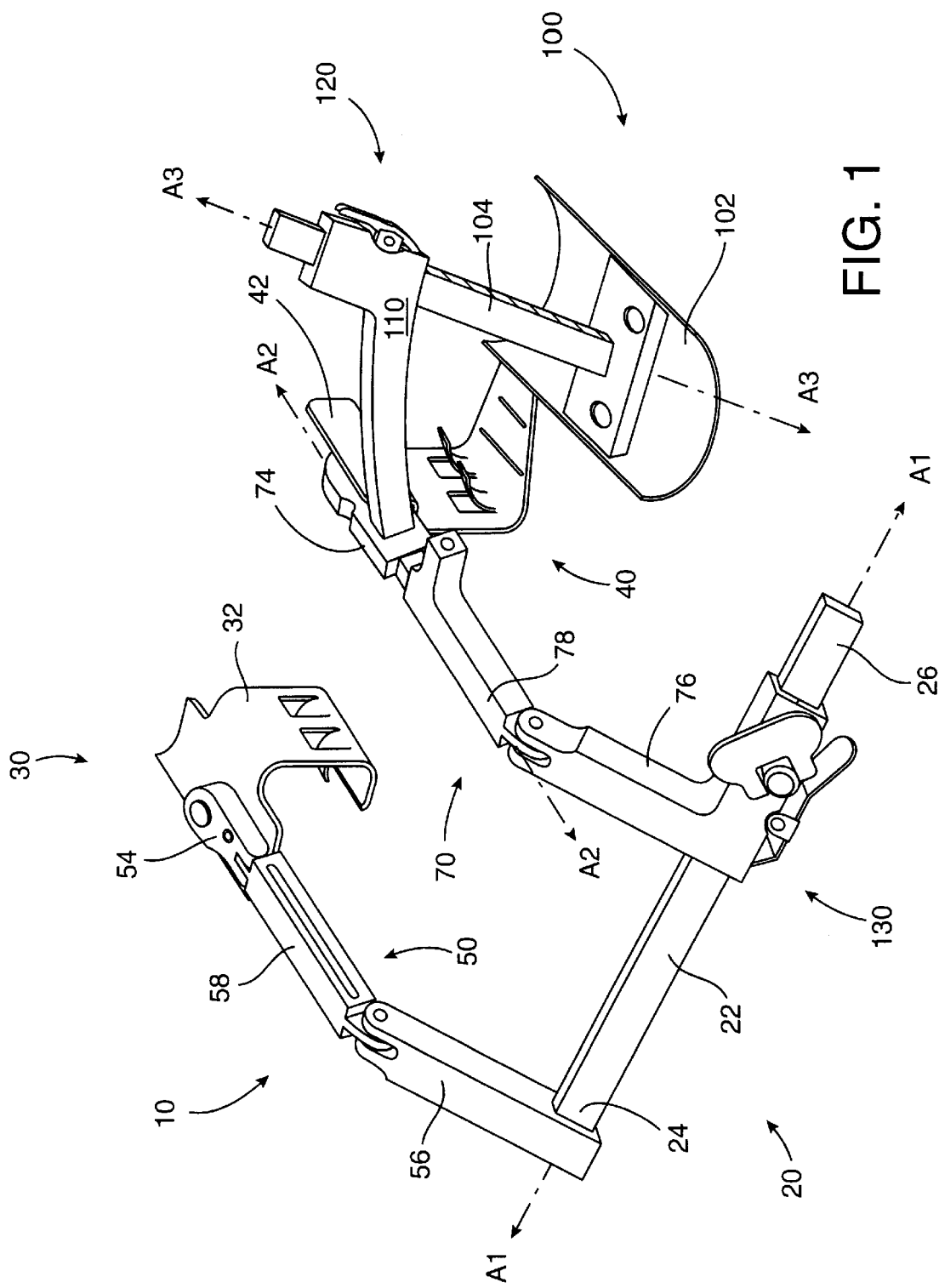
FIG. 1 is a perspective view of a surgical retractor constructed according to a preferred embodiment of the invention, the retractor configured for use in lifting one side of an incision formed in a patient's body with respect to an opposite side of the incision.
Figure 2:
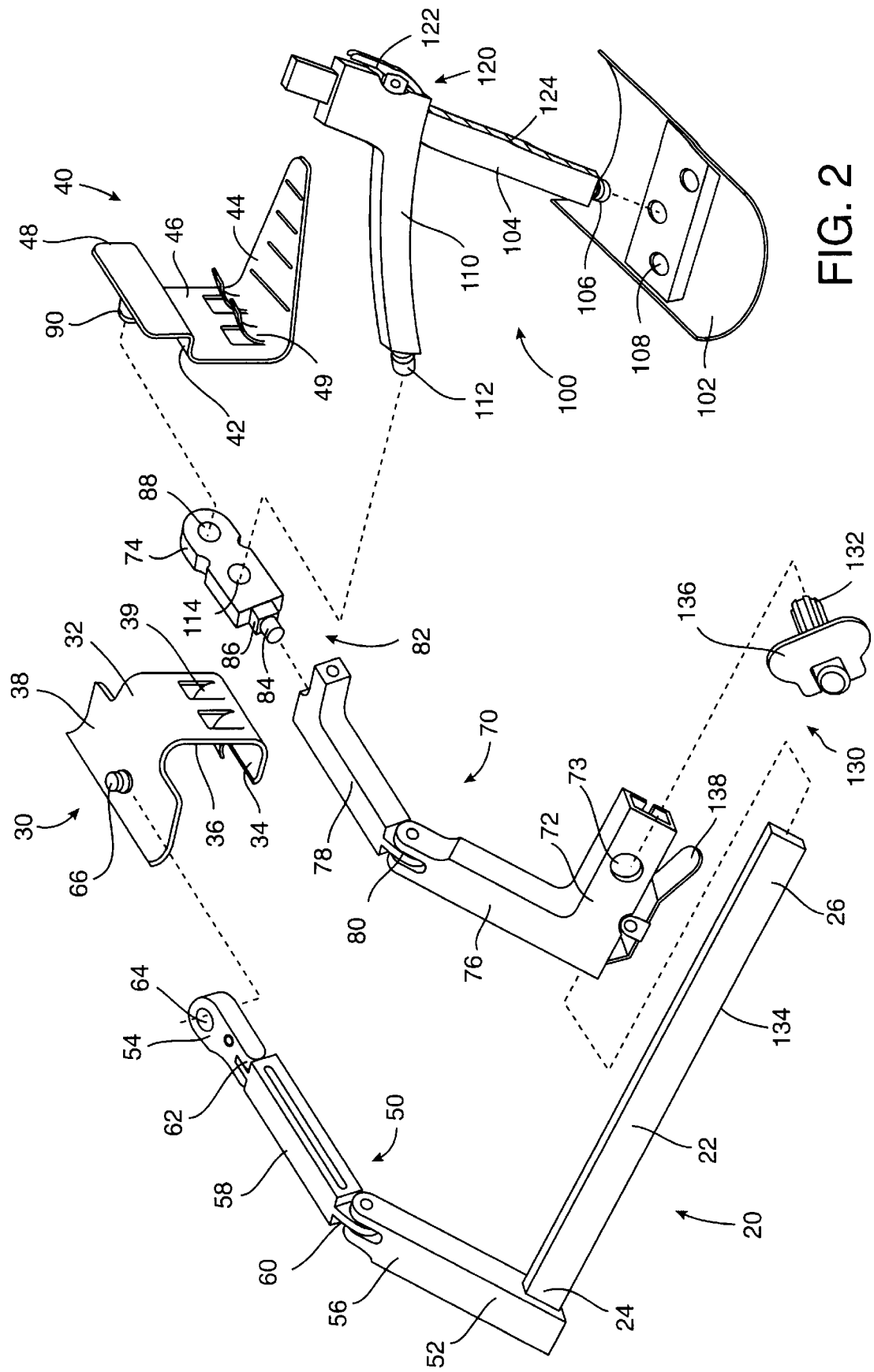
FIG. 2 is an exploded perspective view of the retractor of FIG. 1.

With reference to FIGS. 1 and 2, a surgical retractor constructed according to a preferred embodiment of the invention is indicated generally by the reference numeral 10. The retractor 10, as depicted in FIG. 1, is configured to lift one side of an incision formed in a patient's body with respect to an opposite side of the incision, for example, an incision formed between adjacent ribs in a patient's chest. The retractor 10 includes a frame 20 and first and second retractor blades 30, 40 configured to engage opposite sides of the incision. The retractor blades 30, 40 are coupled to the frame 20 so as to be relatively movable toward or away from each other. A foot 100 for contacting the patient's body adjacent the incision is also coupled to the frame 20.

In the preferred and illustrated embodiment, the frame 20 comprises a frame member 22 which may be in the form of an elongated bar having opposite ends 24, 26. The retractor blades 30, 40 are coupled to the frame member 22 so as to be relatively movable toward or away from each other along a first axis A1. The frame member 22 preferably is straight, although it may have a curved, bent or other configuration.

The preferred configuration of the first retractor blade 30 comprises a generally C-shaped blade element 32 having a lower retraction surface 34, a central retraction surface 36, and an upper end 38. The upper end 38 of blade element 32 is preferably shaped with a curvature extending away from the lower surface 34 to allow pivoting motion of the blade with minimal trauma to tissue. The illustrated blade element 32 is configured to engage a portion of a rib and adjacent body tissue located at one side of the incision. To facilitate such engagement, the retraction surface 36 of the blade element 32 is preferably provided with one or more indexing tabs 39 which project away from surface 36 and effectively divide the surface into upper and lower sections. In use, the section of the retraction surface 36 disposed below the tabs 39 (as viewed in FIG. 1) cooperates with surface 32 to receive and retract a portion of a patient's rib, while the section of the retraction surface 36 disposed above the tabs 39 cooperates with surface 32 to receive and retract soft tissue of the chest wall located anterior to the ribs.

The preferred configuration of the second retractor blade 40 comprises a generally L-shaped blade element 42 having a lifting surface 44, a retraction surface 46, and an upper end 48. The illustrated blade element 42 is designed to lift one side of the incision with respect to an opposite side of the incision and is configured to engage a portion of a rib and adjacent body tissue located at the side of the incision to be lifted. The retraction surface 46 of the blade element 42 is preferably provided with one or more indexing tabs 49 which are formed the same as tabs 39 of blade element 32 and project away from surface 46 to define upper and lower sections thereof. Thus, in use, the section of the retraction surface 46 disposed below the tabs 49 receives and retracts and lifts a patient's ribs while the section of the retraction surface 46 disposed above the tabs 49 receives and retracts soft tissue of the chest wall located anterior to the ribs.

The first and second retractor blades 30, 40 are coupled to the frame 20 by coupling structure extending between each blade and the frame. In the preferred construction, the blade element 32 is coupled to the frame member 22 by a coupling arm indicated at reference numeral 50 having one end 52 secured to the frame member 22 and another end 54 detachably secured to the blade element 32. The coupling arm 50 preferably has an articulated construction and includes an inner portion 56 adjacent frame member 22 and an outer portion 58 pivotally attached to portion 56 by a hinge 60. The outer portion 58 pivots relative to the inner portion 56 about an axis passing through the hinge 60 which, in the illustrated embodiment, is generally parallel to the axis A1. The end 54 of the coupling arm is pivotally attached to the outer portion 58 by a hinge 62 so as to pivot about an axis generally parallel to that of hinge 60. The end 54 is provided with an opening 64 configured for detachably securing a mounting pin 66 provided on the blade element 32. Any suitable detachable connection may be used to mount the blade element 32 to the end 54 of the coupling arm 50. For example, the opening 64 may contain a spring-biased detent (not shown) that snaps into a circumferential groove provided on the mounting pin 66. Other mechanisms may be used to lock the blade element 32 to the coupling arm 50, for example, a bayonet-type connection. The blade element 32 is preferably rotatable relative to the end 54 about an axis passing through pin 66 to positively engage the ribs and soft tissue and evenly distribute the load thereon.

The blade element 42 is coupled to the frame member 22 by a coupling arm indicated at reference numeral 70. The coupling arm 70 has one end 72 movably coupled to the frame member 22 and an opposite end formed as a link member 74 configured to detachably mount the blade element 42. The coupling arm 70 preferably has an articulated construction and includes an inner portion 76 located adjacent frame member 22 and an outer portion 78 pivotally attached thereto by a hinge 80. The outer portion 78 pivots relative to the inner portion 76 about an axis passing through the hinge 80 which, in the illustrated embodiment, is generally parallel to the axis passing through the hinge 60 and the axis A1. The link member 74 has an opening 88 configured for detachably receiving a mounting pin 90 provided on the blade element 42. The pin 90 of the blade element 42 may be attached to the link member 74 in the same manner that pin 66 of blade element 32 is attached to the opening 64 of coupling arm 50. The blade element 42 also is preferably rotatable relative to the link member 74 about an axis passing through the mounting pin 90 to positively engage and evenly distribute the load on the ribs and soft tissue.

The link member 74 is attached to the outer portion 78 of the coupling arm 70 so as to be rotatable relative thereto, and is preferably provided with a rotational locking mechanism indicated at reference numeral 82 for selectively preventing or permitting rotation of the link member relative to the coupling arm 70. In the illustrated embodiment, the link member 74 is rotatable when the retractor is in lift and spread mode but non-rotatable when the retractor is in spread mode.

The preferred rotational locking mechanism 82 comprises a mounting pin 84 and a square shoulder 86 extending from the link member 74. The outer portion 78 of the arm 70 is provided with an opening (not shown) that removably receives the mounting pin 84 so as to allow the link member 74 and blade element 42 to rotate about an axis A2 which is transverse, and preferably perpendicular to the axis A1. The mounting pin 84 may be detachably received in the portion 78 by any suitable connection. For example, a spring-biased detent (not shown) may be provided in the opening in portion 78 which snaps into a circumferential groove located on pin 84. Rotation of the link member 74 about axis A2 occurs as the blade element 42 lifts one side of the incision with respect to the other side, as described further below. In order to lock the link member 74 and blade 42 against rotation about the axis A2, the link member is pushed toward arm 70 until the shoulder 86 seats in a square portion of the opening (not shown) in the outer arm portion 78. The link member 74 preferably can be rotationally locked in the outer arm portion 78 at different positions about the axis A2.

Although the link member 74 is removably attached to the frame member 22, it may instead be irremovably attached thereto but still shiftable between the rotatable and non-rotatable positions described above. Further, while the link member 74 is preferably shiftable between these two positions with respect to the frame member 22, it may alternatively be fixed in a rotatable position if the retractor is to be used only for lifting and spreading, or a non-rotatable position if the retractor is to be used only for spreading.

The coupling arms 50, 70 are preferably articulated as shown in the Figures in order to permit the retractor blades to be moved with respect to the frame about the axis A1 by relative pivoting of the inner and outer portions of the arm. This permits adjustment of the frame member 22 with respect to the retractor blades which may be useful, for example, to accommodate patients having different chest sizes or configurations, e.g., barrel-shaped or flat torsos. However, it will be appreciated that non-articulated coupling arms could be used to couple one or both retractor blades to the frame if adjustability is neither required nor desired.

A stabilizing foot indicated by reference numeral 100 is coupled to the frame member 22 and includes a foot plate 102 configured to contact a patient's body adjacent an incision in which the blade elements 32, 42 are positioned. The foot plate 102 preferably has a concave interior and a convex exterior to minimize trauma to the patient's body; however, the foot plate may be flat if desired. The foot plate 102 engages the exterior surface of the patient's body to provide a base that cooperates with the blade element 42 to lift one side of the incision. The foot 100 is coupled to the frame 20 by coupling structure extending between the foot plate 102 and the frame member 22. The preferred coupling structure comprises a column 104 having an end 106 configured to be detachably received in an opening 108 provided in the foot plate 102. The foot plate 102 is attached to, or alternatively formed integrally with, a bracket provided with a plurality of openings 108 to allow adjustment of the relative position of the foot plate and the column 104. The openings 108 may include any suitable mechanism for attaching the column, for example, a spring-biased detent which engages a groove located on the end 106 of column 104. If desired, however, the foot plate may be irremovably attached to the column 104. Additionally, while the foot plate 102 is preferably fixed to the column 104 so as to move therewith on the chest during lifting, the foot plate could instead be pivotally attached to the column so that the foot plate remains in place on the chest and the column pivots during lifting.

The column 104 is movably engaged with a beam 110 having an end 112 removably attached to an opening 114 formed in the link member 74. The engagement between the beam end 112 and the opening 114 is preferably the same as between the mounting pin 90 of the blade element 42 and the opening 88 in the link member 74. While in the preferred embodiment the foot 100 is coupled to the frame member 22 by the link member 74 and the coupling arm 70, it may instead be coupled to another component of the retractor, for example, the coupling arm 50 or either retractor blade 30, 40. The column 104 is slidably engaged with the beam 110 via a channel 114 formed at one end of the beam 110 in order to adjust the position of the foot plate 102. The column 104 is slidable relative to the beam 110 (and thus the frame member 22) along an axis A3 which is transverse to the axis A1. In the preferred embodiment, the foot plate 102 is adjustable relative to the frame member 22 in a linear direction, and the axis A3 is generally perpendicular to the axes A1 and A2; however, the direction along which the foot plate 102 is adjusted and the angular relationship of the axes may be varied from that shown.

The foot 100 is provided with a locking mechanism indicated at reference numeral 120 for locking the relative position of the column 104 and the beam 110. The preferred mechanism 120 prevents relative movement of the column 104 and the beam 110 in one direction and includes a pivoting pawl 122 carried by the beam 110 which is engaged with a rack 124 provided on the column 104. The foot plate 102 is moved into engagement with the surface of a patient's body by sliding the column 104 relative to the beam 110 along the axis A3, the pawl 122 riding along the teeth of rack 124. The position of the foot plate 102 thus may be adjusted to accommodate different size patients. If desired, a pinion could be provided to move the column 104 relative to the beam 110. The foot plate 102 and column 104 are prevented from moving back along the beam 110 by the pawl 122 and rack 124. It will be recognized, of course, that other suitable locking mechanisms may be used to prevent the foot plate 102 from moving relative to the frame member 22, for example, a pin inserted into an opening in the beam 110 which is may be aligned with one of a plurality of openings in the column 104.

As described above, the first and second retractor blades 30, 40 are coupled to the frame 20 so as to be relatively movable along the axis A1. An actuator indicated at reference numeral 130 is provided to impart relative movement to the blades. In the preferred embodiment, the actuator 130 comprises a pinion 132 carried by the coupling arm 70 which interacts with a rack 134 provided on the frame member 22 to impart relative movement to the blade elements 32, 42. While a rack and pinion actuator is preferred, other mechanisms may be used to impart relative movement to the retractor blades.

As seen in FIGS. 1 and 2, the end 72 of the arm 70 is formed as a sleeve slidably positioned on the frame member 22, and the pinion 132 is disposed through an opening 73 formed in the sleeve. The pinion is rotated via a knob 136 to move the coupling arm 70 and blade element 42 away from the coupling arm 50 and blade element 32, such movement taking place along the axis A1. The actuator 130 is provided with a pivotally mounted pawl 138 engaged with the teeth of the rack 134 to prevent the coupling arm 70 from backing up toward the coupling arm 50 during retraction. The pawl 138 is pressed to disengage the teeth of the rack 134 in order to move the coupling arm 70 toward the arm 50 along the axis A1. While a pawl and ratchet actuator is illustrated, other mechanisms may be used to prevent the coupling arm 70 from moving toward the coupling arm 50, for example, a pin and mating openings respectively provided on the frame member 22 and the coupling arm 70. The pawl and ratchet actuator is preferred because it provides high resolution and precise control of retraction during use.

In the preferred embodiment, the coupling arm 50 and the blade element 32 are fixed from moving relative to the frame member 22 along the axis A1, while the coupling arm 70 and the blade element 42 are moved along the frame member upon actuation of the actuator 130. It should be recognized, however, that other constructions may be utilized to achieve relative movement of the retractor blades with respect to the frame. For example, both retractor blades could be coupled to the frame and driven in unison toward or away from each other.

Figure 5:
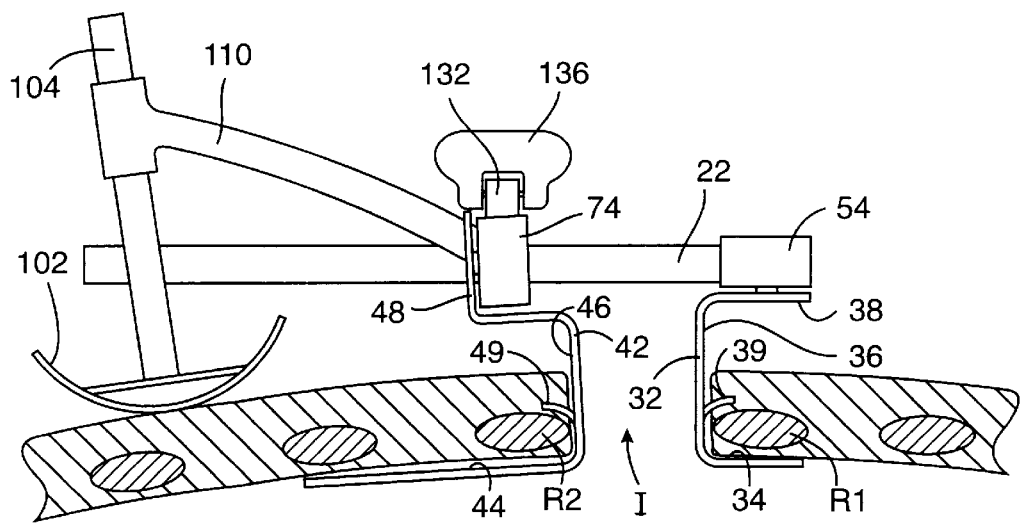
FIG. 5 is a sectional schematic view showing the retractor of FIG. 1 inserted into an incision formed in a patient's body.

Referring to FIG. 5, the retractor 10 of FIG. 1 is shown positioned in an incision I formed in the thorax of a patient's body, the size of the incision being exaggerated for sake of clarity. In use, the blade elements 32, 42 are either engaged with opposite sides of the incision and then attached to the coupling arms 50, 70, or the coupling arms and attached blade elements are moved close together to allow the blade elements to be engaged in the incision. As shown, the blade element 32 is engaged with one side of the incision I such that lower retraction surface 34 engages the interior of the chest wall and retraction surface 36 engages the edge of the incision I. The lower portion of the retraction surface 36 (i.e., below the tab 39) engages a portion of a rib R1 and the upper portion of the surface (i.e., above the tab 49) engages soft tissue of the chest wall adjacent the rib R1. Similarly, the blade element 42 is engaged with an opposite side of the incision such that the lifting surface 44 is disposed against the interior of the chest wall. The retraction surface 46 of the blade element 42 is engaged with the edge of the incision I, the lower portion of the surface (i.e., below the tab 49) engaging a portion of a rib R2 and the upper portion of the surface (i.e., above the tab 49) engaging soft tissue of the chest wall. The retractor blade elements 32, 42 are disposed in the intercostal space defined between ribs R1 and R2 while the foot plate 102 is positioned against the outer surface of the chest wall, the locking mechanism 120 preventing the foot plate from moving away along the axis A3.

Figure 6:
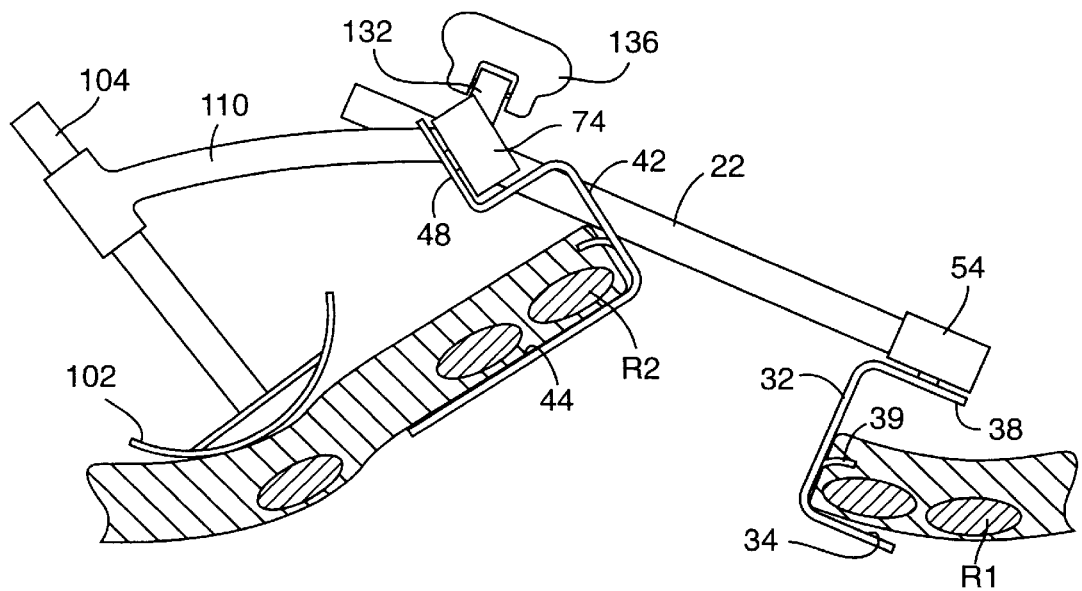
FIG. 6 is a sectional schematic view showing the retractor of FIG. 5 being used to lift one side of the incision with respect to the other side of the incision.

Referring to FIG. 6, the retractor 10 is shown after the actuator 130 has been actuated to impart relative movement to the blade elements 32, 42, which, in the preferred embodiment, is carried out by moving blade element 42 away from blade element 32. Rotation of the pinion 132 via knob 136 drives the coupling arm 70 and the blade element 42 relative to the frame member 22 along axis A1. This forces the foot plate 102 against the outer surface of the chest wall. The foot plate 102 preferably assumes a secure position on the chest with substantially no significant slippage. In addition, rotation of the pinion 132 exerts a force against the coupling arm 50 and the blade element 32 which tends to rotate the blade element 32 a slight amount upward against the edge of the incision. This causes the frame member 22 to rotate a slight amount as it is fixed to the coupling arm 50.

As the pinion 132 is rotated and the coupling arm 70 moves along the frame member 22, the link member 74 rotates about the axis A2 (in a counter-clockwise direction as viewed in FIGS. 5 and 6). As a result, the blade element 42 rotates in the same direction to lift the side of the incision and rib R2 with respect to the opposite side of the incision. The beam 104, column 110 and foot plate 102 also rotate as they are rigidly fixed to the link member 74, the foot plate rocking on the chest as the one side of the incision is lifted. Thus, rotation of the pinion moves coupling arm 70 and blade element 42 away from the coupling arm 50 and blade element 32, and also rotates the blade element 42 about the axis A2 with respect to the frame member 22. Once the side of the incision and the rib R2 have been sufficiently retracted and lifted, for example, to permit access to an internal mammary artery (not shown) located on the interior of the chest wall, the blade elements 32, 42 remain in position due to the pawl 138 engaging the rack 134 on frame member 22. As can be seen in FIG. 6, the retractor lifts multiple ribs to provide ample access to the interior of the chest.

Figure 3:
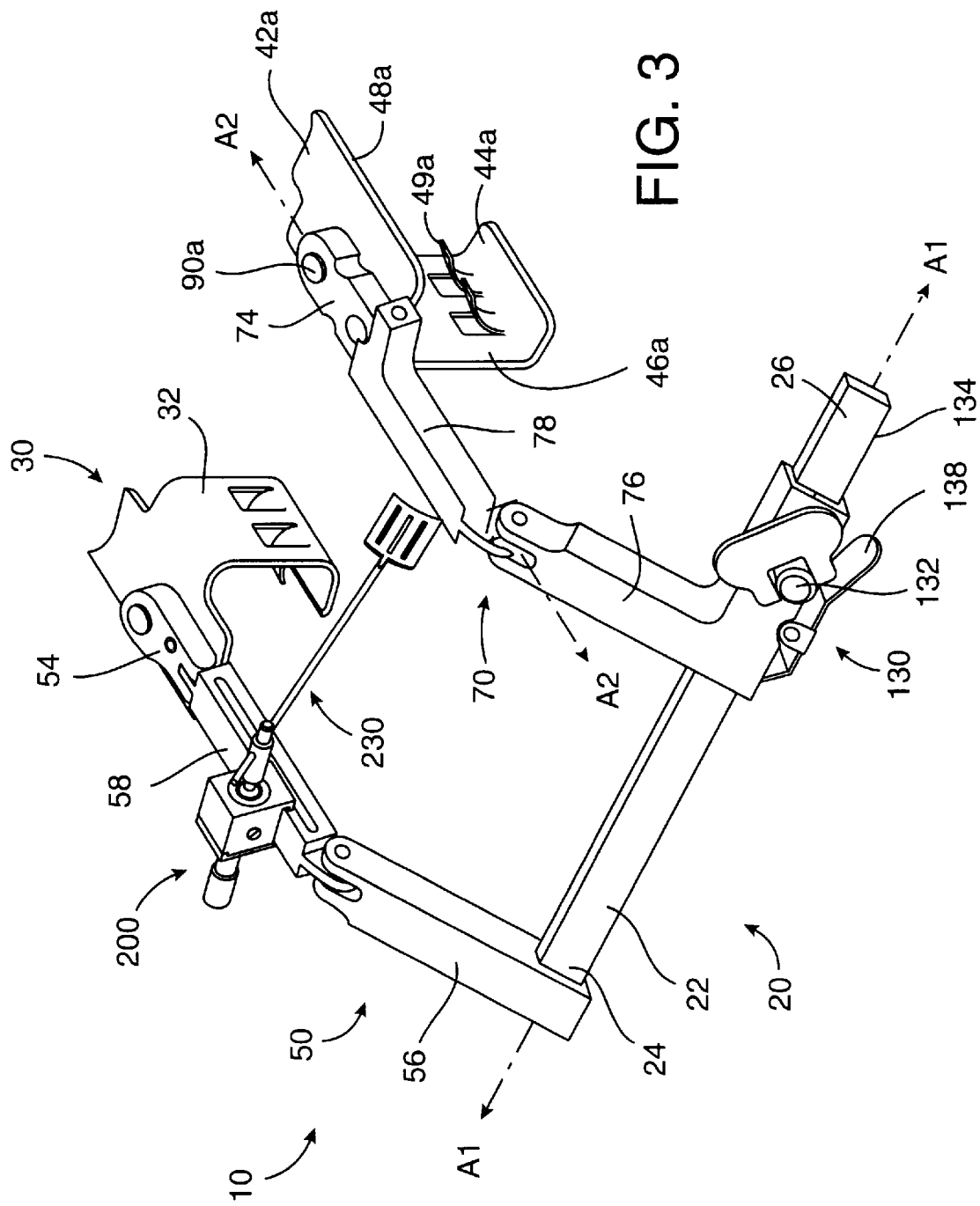
FIG. 3 is a perspective view of the surgical retractor of FIG. 1 configured for use in spreading the opposite sides of an incision formed in a patient's body, wherein an accessory clamp supporting an instrument is attached to the retractor.
Figure 4:
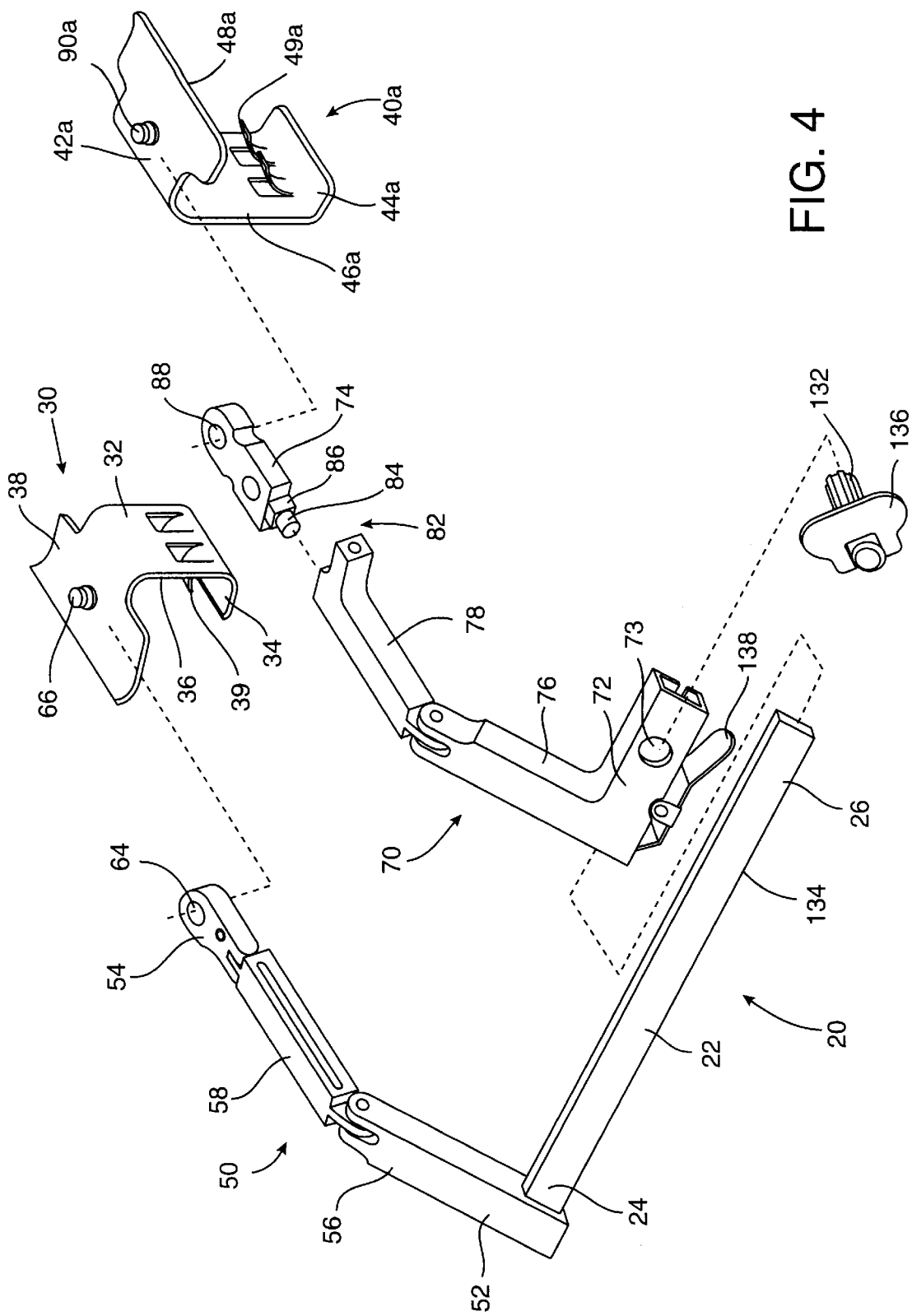
FIG. 4 is an exploded perspective view of the retractor of FIG. 3, without the accessory clamp.

In some procedures, it may be desirable, either subsequent to or in lieu of lifting one side of the incision, to spread the ribs substantially along the axis A1. Referring to FIGS. 3 and 4, the retractor 10, according to the preferred embodiment of the invention, can be easily configured in spread mode to retract the sides of the incision along the axis A1. In order to switch the retractor to spread mode while it is located in the incision, the tension exerted on the blade elements 32, 42 is released by depressing the pawl 138 to back up the coupling arm 70 and blade element 42 along the frame member 22. This rotates the link member 74 and blade element 42 back toward the opposite side of the incision, thereby lowering the side of the incision that is shown raised in FIG. 6. The resulting orientation of the retractor 10 is shown in FIG. 5. Next, the foot 100 is removed by disconnecting the beam 110 from the link member 74. Also, if desired, the blade 40 and the blade element 42, which has a substantial lifting surface 44, may be replaced with blade 40a having a blade element 42a comprising indexing tabs 49a, a lower retraction surface 44a, a central retraction surface 46a, an upper end 48a, and a mounting pin 90a configured to detachably engage the opening 88 in the link member 74. See FIGS. 3, 4, 7 and 8. The retraction surface 46a may be divided into upper and lower portions by one or more tabs 90a. The link member 74 is rotated to an alternative position with respect to the coupling arm 70 (as shown in FIG. 3) in order to mount the blade element 42a. The link member 74, however, may be used in different positions depending on the particular application.

The rotational locking mechanism 82 is adjusted to prevent the link member 74 from rotating with respect to the coupling arm 70. This is achieved by engaging the square shoulder 86 of the link member with the recess or socket (not shown) formed in the outer portion 78 of arm 70. This fixes the link member 74 and the blade element 42a rotationally with respect to the coupling arm 70 and the frame member 22. The pinion 132 of actuator 130 is then rotated to move the blade element 42a away from the blade element 32 along the axis A1. This moves the blade elements from the position shown in FIG. 7 to that shown in FIG. 8, wherein the opposite sides of the incision I have been spread in a superior-inferior direction. The blade element 32 and the frame member 22 also move along axis A1 to exert a retraction force on rib R1, as can be seen in FIG. 8. When used in spread mode as shown in FIG. 8, the retractor permits any of a variety of procedures to be performed by accessing the thoracic contents through the incision, for example, anastamosis of arterial conduits to the coronary arteries, mitral valve repair or replacement, etc., such procedures being performed with or without the aid of endoscopic viewing instruments.

Figure 9A:
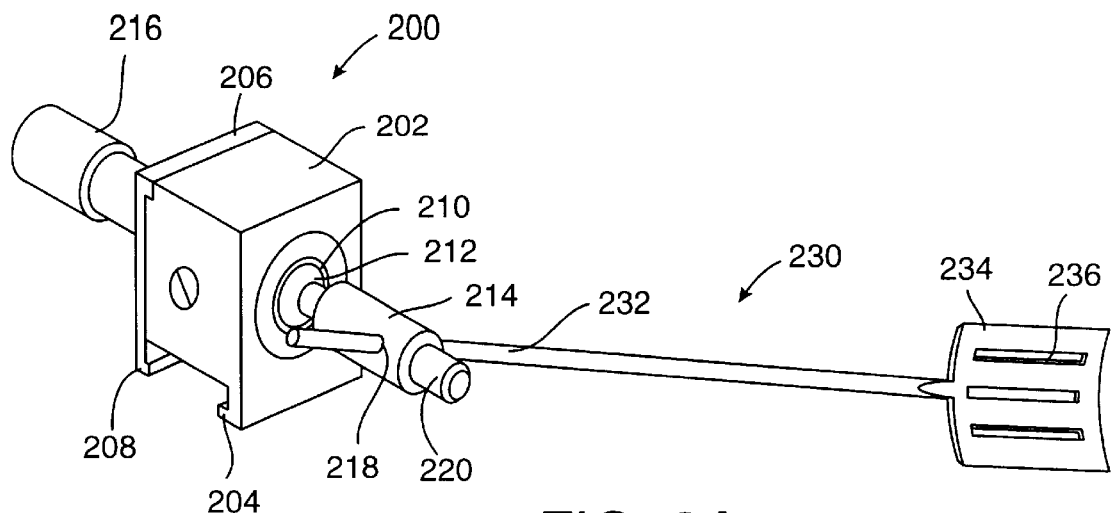
FIGS. 9A is an enlarged perspective view of the accessory clamp and instrument shown in FIG. 3.

FIG. 9A shows an accessory clamp indicated by reference numeral 200 in FIG. 3 which is configured for removable attachment to the retractor 10. As seen in FIG. 3, the clamp 200 is secured to the coupling arm 50; however, it will be recognized that the clamp 200 may be attached to another component of the retractor 10, for example, the coupling arm 70 or the frame member 22. Further, while it is preferred to mount the clamp 200 so as to be removable from the retractor, it could alternatively be permanently fixed thereto. The clamp 200 removably receives an instrument 230 which, for example, may take the form of a cardiac retraction implement including a handle 232 and a retraction blade 234. The illustrated blade 234 has a plurality of openings 236 and may be used to retract or otherwise manipulate the heart, tissue adjacent the heart, etc.

The preferred construction of the clamp 200 comprises a block 202 provided with a leg 204, and a plate 206 provided with a leg 208. The block 202 and the plate 206 are adjustable relative to each other in order to clamp a component of the retractor 10, for example, the coupling arm 50, between the legs 204, 208. The block 202 has a socket 210 in which is received a ball 212 carried by an instrument mounting member 214. A screw 216 passes through aligned openings formed in the plate 206 and the block 202 and engages the ball 212 of member 214. Rotating the screw 216 moves the plate 206 against the block 202 to clamp a retractor component therebetween, and also fixes the position of the member 214 relative to the block 202. The handle 232 of the instrument 230 is slidably received in an opening 218 passing through the member 214, and a set screw 220 is preferably used to engage the handle 232 to fix the instrument 230 relative to the clamp 200. While the set screw 220 is preferred to secure the instrument to the member 214 of clamp 200, an alternative mechanism may be used.

Figure 9B:
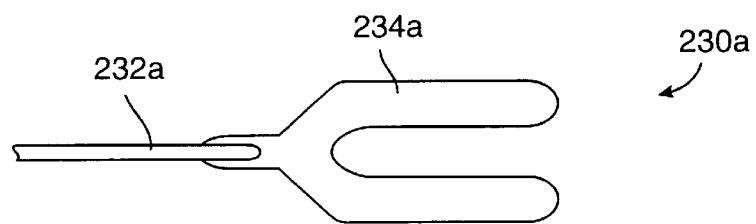
FIGS. 9B and 9C are perspective views of additional instruments that may be used with the accessory clamp of FIG. 9A.
Figure 9C:
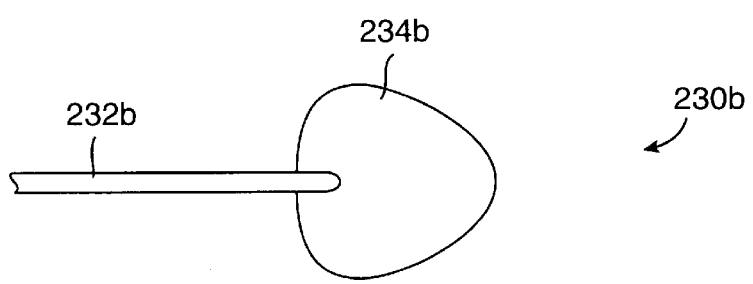

FIGS. 9B and 9C depict alternative instruments which may be used to retract, move or manipulate the heart or tissue adjacent the heart. The retraction implement 230a includes a shaft 232a receivable in the opening 218 of member 214 of the clamp 200 and a blade 234a configured to manipulate the heart. For example, the blade 234a may be used to move or reposition the heart to present different areas for access through the incision during a multiple bypass procedure. The retraction implement 230b includes a shaft 232b which is receivable in the opening 218 of member 214, and a blade 234b which is configured to manipulate the heart. The blade 234b comprises a pair of prongs 236a which may used to retract a portion of the heart. The retraction implements 230, 230a, 230b preferably are formed from a material which permits the shafts and/or blades to be bent into various configurations. A suitable material is 304 stainless steel. The blades 234, 234a, 234b may be provided with a friction-enhancing material, e.g., gauze, DACRON, GORETEX or suction cups, or, alternatively, the surface of the blade may be roughened or otherwise textured to grip and hold the heart during a surgical procedure.

Figure 10:
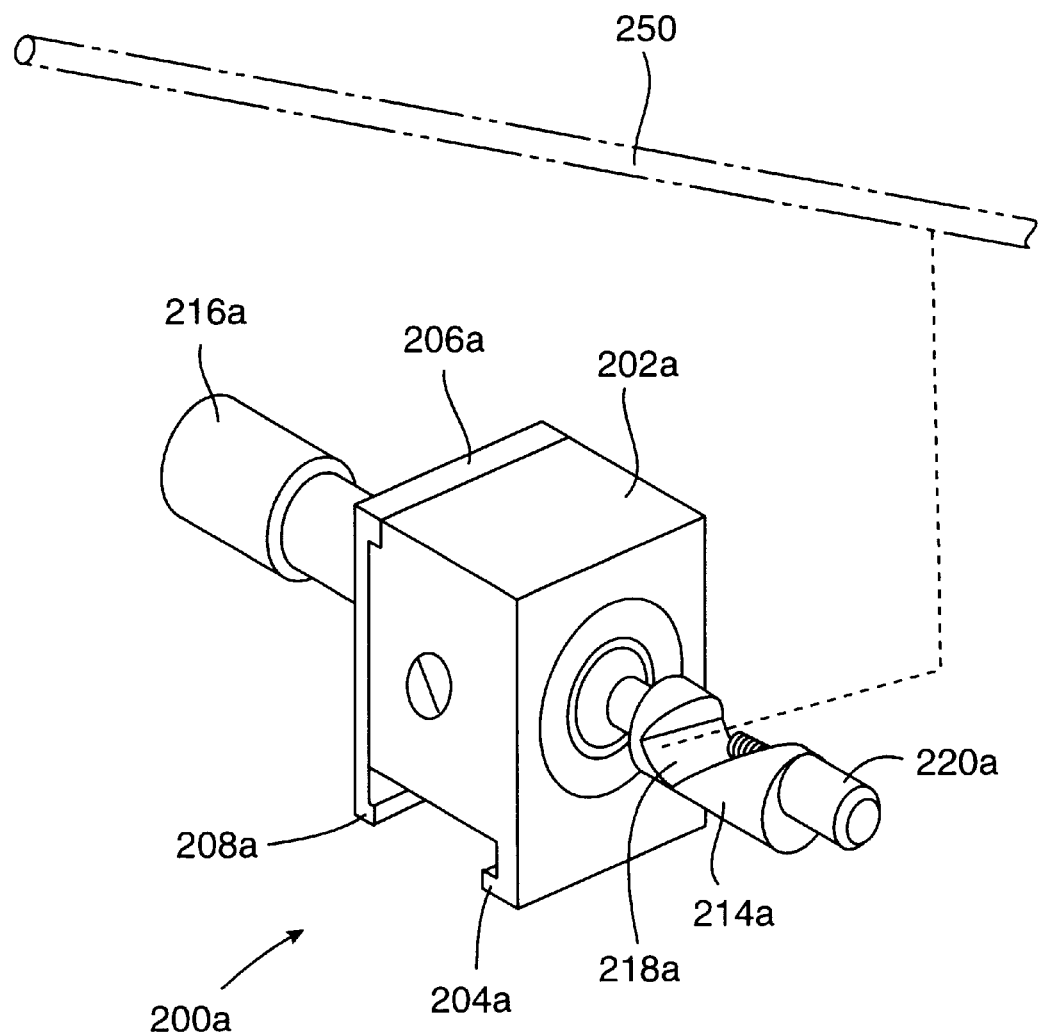
FIG. 10 is a perspective view of an accessory clamp constructed according to an alternative embodiment of the invention and various auxiliary instruments which may be supported by the clamp.

FIG. 10 illustrates an alternative accessory clamp 200a which is adapted to mount various types of auxiliary instruments which may be used in carrying out surgical procedures. The clamp 200a is similar to clamp 200 and comprises a block 202a with a leg 204a and a plate 206a with a leg 208a. The block 202a and the plate 206a are adjustable relative to each other in order to clamp a component of the retractor 10 between the legs 204a, 208a. The clamp 200a has an instrument mounting member 214a provided with a recess 218a configured to receive a surgical instrument 250a (depicted schematically in phantom). The instrument is received in the recess 218a and held therein by a set screw 220a. The screw 216a is rotated to move the plate 206a against the block 202a and to fix the position of the member 214a relative to the block 202. The surgical instrument 250 may be any of various devices, including retraction or stabilization devices such as those shown in FIGS. 9A–9C, devices for visualizing and/or illuminating the surgical site, aspirating devices connected to a source of vacuum in order to remove fluid or debris from the site, blower devices for irrigating the site with air, C02 or other fluids, etc.

Figure 11:
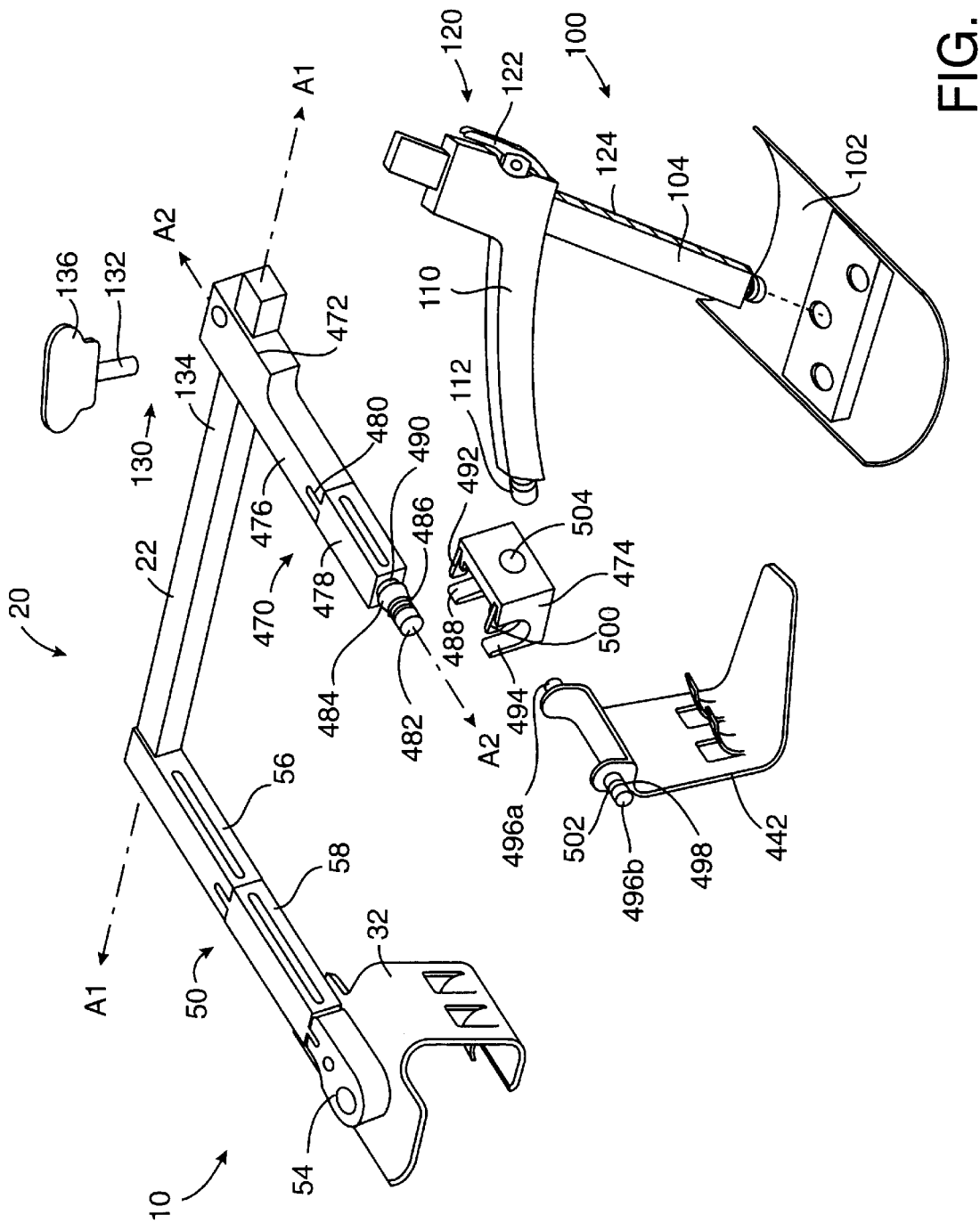
FIG. 11 is a perspective view of a retractor blade and blade coupling component constructed according to an alternative embodiment of the invention.

FIG. 11 illustrates an alternative embodiment of a retractor 10 which is constructed the same as the retractor described above with the exception of the coupling arm that is movably disposed on the frame member and rotatably mounts one of the retractor blades. The coupling arm 470 has one end 472 movably coupled to the frame member 22 and an opposite end in the form of a member 474 configured to detachably mount a blade element 442 and the foot 100. The coupling arm 470 preferably has an articulated construction including an inner portion 476 attached to an outer portion 478 by a hinge 480. The outer portion 478 has a plug 482 which engages the member 474 in two positions, one permitting and one preventing rotation of the member 474 about the axis A2. The plug 482 has a pair of parallel annular channels 484, 486 each of which engages a socket 488 provided in the member 474. The inner channel 484 has one or more detents 490 so that when engaged with the socket 488 the member 474 will not rotate about the axis A2. When the outer channel 486 is engaged with the socket 488 the member 474 is free to rotate about the axis A2. The member 474 has a spring latch 492 which locks the plug 482 within socket 488.

The member 474 is provided with a second socket 494 which receives either of plugs 496a, 496b carried by the blade element 442 to permit reversal of the position of the blade element. Each of the plugs 496a, 496b has an annular channel 498 which engages the socket 494 and is held therein by a spring latch 500. The annular channels 498 have a detent 502 which prevents the blade element 442 from rotating relative to the socket 494. The member 474 is provided with an opening 504 configured for detachably receiving the end 112 of the beam 110 of the foot 100, preferably in the same manner that end 112 is attached to the opening 84 of link member 74 described above. Accordingly, in lift mode, the socket 488 of member 474 is engaged with the outer annular channel 486 of plug 482 to permit rotation of the blade element 442 and foot 100 about axis A2. In spread mode, the socket 488 is engaged with the inner annular channel 484 of plug 482 to prevent rotation of the blade element 442 and foot 100 about axis A2.

A retractor constructed according to a preferred embodiment of the invention may be used to first lift one side of an incision relative to the other side in an anterior direction and then, without having to remove the retractor from the incision, to spread the sides of the incision in a superior-inferior direction. However, it will be appreciated that the retractor of the invention may be used solely in lift mode (FIGS. 1 and 2) or spread mode (FIGS. 3 and 4).

In an exemplary application of the invention, the retractor is used to lift one side of an incision located in the intercostal space between adjacent ribs (FIGS. 5 and 6) in order to harvest the left or right internal mammary artery (IMA—not shown) from the raised side for subsequent use in a coronary artery bypass procedure. The retractor may then, if desired, be used to spread the sides of the incision (FIGS. 7 and 8) and provide access to the heart in order to perform an anastamosis of the IMA to an occluded coronary artery. Procedures for harvesting or taking down the internal mammary arteries, placing the patient on cardiopulmonary bypass, and anastamosing the IMA to a coronary artery are described in commonly owned, co-pending patent application Ser. No. 08/486,941, (Now U.S. Pat. No. 5,799,661), the subject matter of which is incorporated herein by reference.

Figure 12:
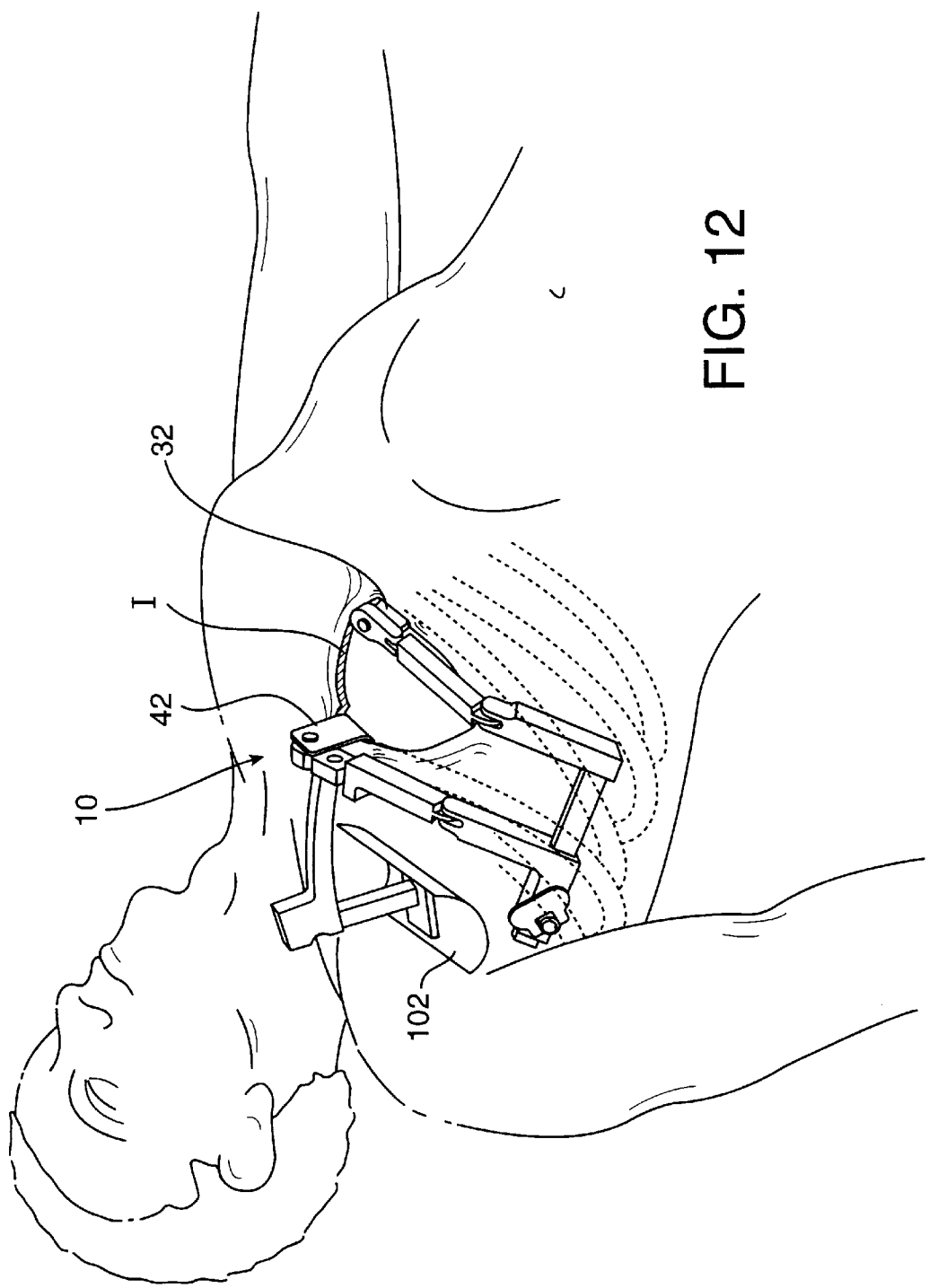
FIG. 12 is a perspective schematic view of the retractor of FIG. 1 being used to lift one side of an incision formed in a patient's chest so as to provide access to the internal mammary artery.

FIG. 12 illustrates schematically use of the retractor 10 to lift the superior side of an incision I in order to harvest the right IMA. The blade elements 32, 42 are pressed to the sides of the incision and the foot plate 102 is disposed against the outer surface of the chest wall, the blade element 42 engaging the side of the incision to be lifted. The actuator 130 is actuated as described above so that the blade element 42 lifts the side of the incision a sufficient amount to provide sufficient access to the underside of the chest wall to permit harvesting the right IMA (not shown). A section of the IMA may be transected from the chest wall and removed from the body to provide a free graft the ends of which are prepared for anastamosis to the aorta and an occluded coronary artery. Alternatively, the IMA may be transected from the chest wall to provide a single end which is prepared for anastamosis to the coronary artery. The retractor 10 may be placed in spread mode to retract the incision and facilitate anastamosis of the transected IMA. The accessory clamp of FIG. 9A and instruments of FIGS. 9B and 9C may be used to retract or manipulate the heart to different positions to carry out the anastamosis.

The retractor of the invention may be used in additional applications requiring access to the heart, lungs, or great vessels. For example, the retractor may be used to perform a proximal anastamosis of one or more arterial conduits to the aorta. The conduits, for example, the right or left IMA, may be harvested from other areas of the body and prepared in a conventional fashion for anastamosis, either prior to or simultaneously with placing the patient on cardiopulmonary bypass. The retractor 10 is engaged with opposite sides of the incision in the chest wall so as to allow access to the heart. The blade elements are pressed to the sides of the incision, the foot plate is disposed against the outer surface of the chest wall, and the actuator is actuated to lift the side of the incision a sufficient amount to provide access to the aorta.

The surgeon utilizes one or more arterial conduits (either harvested from the body or artificial) that have been prepared for anastamosis, the number of conduits corresponding to the number of occluded vessels to be bypassed, e.g., three, four or five. Suitable conduits include a saphenous vein graft, the left or right IMA, the inferior epigastric artery, the splenic artery, the subclavian artery, etc. A side biting (or partial occluding) clamp may be used to retract a segment of the ascending aorta targeted for anastamosis. An opening is formed in the retracted segment of the aorta with a scalpel (not shown) and an aortotomy is created. The proximal end of the arterial conduit is then anastamosed to the aorta via a suture which is placed in the tissue by a suitable needle driver or stapling device until the end of the conduit is sufficiently attached to the aorta. The distal end of each arterial conduit is then anastamosed to a coronary artery at a location downstream of the occlusion in the artery, the retractor being used in spread mode to perform this procedure. Suitable procedures for harvesting multiple arterial conduits, placing the patient on cardiopulmonary bypass, and anastamosing the proximal ends of the conduits to the aorta and the distal ends to the coronary arteries are described in commonly owned, co-pending patent application Ser. No. 08/486,941, (now U.S. Pat. No. 5,799,661), the subject matter of which is incorporated herein by reference.

The proximal anastamosis of each conduit to the aorta is preferably performed via direct access through the incision, as is the distal anastamosis of each conduit to the coronary artery. Additionally, the anastamosis is preferably performed by directly viewing the heart and aorta through the retracted incision; however, if desired endoscopic viewing instruments may be utilized to enhance viewing. The heart may be retracted and manipulated to different positions depending on the number and placement of arterial conduits to be anastamosed, and one or more of the cardiac retraction implements described above may be used to position the heart during the procedure.

The retractor is easily modified from its lifting mode to its spreading mode which enables a single retractor to be used to perform two different functions. This reduces the number of components that must be kept on hand and tends to reduce the amount of time required to perform a given procedure. The retractor components are preferably formed of stainless steel and are autoclavable to permit sterilization and reuse of the retractor. Also, a plurality of retractor blades of varying size and shape may be provided to permit a surgeon to select appropriate blades for a given procedure.

It is apparent that the surgical retractor of the invention facilitates retraction of opposite sides of an incision anteriorly and posteriorly (lifting), as well as superiorly and inferiorly (spreading). The retractor preferably has a symmetrical design to allow its use in many different positions relative to a patient's body. For example, in spread mode, the retractor may be used in four different positions. The frame member 22 may be positioned on either the right lateral or right medial side of an incision formed in the right half of a patient's chest, as well as either the left lateral or left medial side of an incision formed in the left half of a patient's chest. To switch the retractor between configurations for use in lateral and medial positions, the blade elements 32, 42 are removed from the retractor, the coupling arm 70 is slid off the frame member 22, and the frame member with coupling arm 50 is rotated 180° about axis A1. The coupling arm 70 with link member 74 is also rotated 180° and then slid onto the frame member 22. The blade elements 32, 42 are then reattached to the coupling arms 50, 70, either before or after they have been inserted in the incision. The frame member 22 of the retractor may be used in either a medial or lateral position in order to permit anterior retraction of particular areas of the heart.

The retractor may also be used in four different positions in lift mode. The frame member 22 may be positioned on either the right medial or right lateral side of an incision formed in the right half of a patient's chest. In the right medial position, the retractor lifts the superior side of an incision formed between adjacent ribs which permits harvesting the proximal segment of the right IMA, while in the right lateral position the retractor lifts the inferior side of the incision which permits harvesting the distal segment of the right IMA.

Similarly, the frame member 22 may be positioned on either the left medial or left lateral side of an incision formed in the left half of a patient's chest. In these two positions the retractor lifts, respectively, the inferior and superior sides of the incision which permits harvesting the distal and proximal segments of the left IMA, respectively. The retractor is switched between configurations for use in lateral and medial positions as described above with respect to the different spread mode position.

The many different positions in which the retractor may be used facilitate a variety of surgical procedures including isolation and harvesting of the right or left interior mammary artery, mitral valve repair and replacement, aortic valve repair and replacement, proximal anastamosis of arterial conduits to the aorta, and any of various other procedures requiring access to the heart, great vessels, lungs or other thoracic contents. Advantageously, the retractor of the invention can be switched between lift mode and spread mode without removing the retractor from the incision in which it is being used. The retractor further allows adjustment for various patient sizes, body shapes and chest wall thicknesses, and has a small profile to minimize interference with surgical instruments and provide enhanced direct and fluoroscopic visualization. The retractor fits into small incisions to allow the performance of minimally-invasive procedures, for example, incisions as small as four centimeters. It should be understood that while the retractor is described in connection with lifting and spreading of ribs, the invention can be used for retraction of various structures and in various body cavities.

Many modifications and variations of the invention will be apparent to those skilled it the art in view of the detailed description of preferred embodiments set forth above. Therefore, the above description should not be taken as limiting the scope of the invention which is defined by the following claims.

What is claimed is:

1. A surgical retractor comprising:

a frame member;

first and second retractor blades coupled to the frame member, the retractor blades having retraction surfaces configured to engage an incision in a patient's body, wherein at least one of the first and second retractor blades is movable with respect to the frame member along a first axis to position the retractor blades toward or away from each other;

a foot coupled to one of the frame member and the first and second blades, the foot having a support surface configured to engage a surface of a patient's body, wherein the foot is adjustable in a linear direction relative to the frame member and traverse to said first axis;

a locking mechanism for locking the foot and the frame member in a selected relative position along said axis which is transverse to the first axis; and an actuator for moving said at least one retractor blade with respect to the other retractor blade along the first axis.

2. The retractor of claim 1, wherein the frame member comprises an elongated bar and the first and second retractor blades are respectively coupled to first and second arms coupled to the bar, one of said arms being movable with respect to the bar along the first axis, the foot being movable in the linear direction along an axis which is transverse to the first axis.

3. The retractor of claim 1, wherein the second blade is rotatable about a second axis which is transverse to the first axis, the foot being coupled to the second blade so that the foot and the second blade rotate together about the second axis.

4. A method of retracting a portion of a patient's body to carry out a surgical procedure, the method comprising steps of:

positioning first and second retractor blades against opposite sides of an incision formed in a patient's body, the first and second retractor blades being coupled to a frame member so as to be relatively movable toward or away from each other along a first axis;

coupling at least one foot to the frame member so as to be adjustable with respect to the frame member in a linear direction along an axis which is transverse to the first axis, the foot having a support surface configured to rest against a surface of the patient's body adjacent the incision;

adjusting the relative position of the foot with respect to the frame member along said linear direction and fixing the foot in a position at which the support surface of the foot rests against the surface of the patient's body adjacent the incision; and imparting relative movement to the first and second blades to simultaneously move the blades apart along the first axis and lift one side of the incision with respect to the other side of the incision.

5. The method of claim 4, further comprising, subsequent to lifting one side of the incision, steps of:

imparting relative movement to the first and second blades to move the blades toward each other along the first axis;

removing the foot from the frame member; and imparting relative movement to the first and second blades to move the blades apart along the first axis and spread the opposite sides of the incision.

6. A rib retractor for spreading apart first and second ribs to create and opening in the patient's chest, comprising:

a frame;

a first blade coupled to the frame;

a second blade coupled to the frame, the second blade being movable toward and away from the first blade, the second blade having a rotatable connector which permits rotation of the second blade relative to the frame;

an actuator for moving at least one of the first and second blades toward the other of the first and second blades;

a foot coupled to at least one of the frame and the first and second blades, the foot having a support surface configured to engage the surface of the patient's chest when lifting the second rib with the second blade; and a locking mechanism which selectively permits and prevents rotation of the rotatable connector, the locking mechanism being movable between a locked position, in which rotation of the rotatable connector is prevented, and an unlocked position, in which rotation of the rotatable connector is permitted, the locking mechanism being in the locked position for spreading the first and second ribs apart without lifting the second rib, the locking mechanism being in the unlocked position to permit rotation of the rotatable connector for spreading the first and second ribs apart and lifting the second rib.

7. The rib retractor of claim 6, wherein:

the foot is linearly movable relative to the frame; and the rib retractor also comprises a locking mechanism selectively permitting and preventing linear movement of the foot relative to the frame.

8. The rib retractor of claim 6, wherein:

the foot is coupled to the second blade so that rotation of the rotatable connector rotates the foot and the second blade together.

9. The rib retractor of claim 6, wherein:

the frame has a first arm and a second arm, the first blade being attached to the first arm and the second blade being attached to the second arm.

10. The rib retractor of claim 9, wherein:

the frame includes an elongate bar, the first and second arms being mounted to the bar, the second arm being movable along the elongate bar toward and away from the first arm along a first axis.

11. The rib retractor of the claim 10, wherein:

the first and second arms each have an inner portion coupled to the bar and an outer portion coupled to the first and second blades, respectively, the inner and outer portions being coupled by a hinge which permits rotation about a second axis generally parallel to the first axis.

12. The rib retractor of claim 6, wherein:

the locking mechanism may be moved from the locked position to the unlocked without removing the first and second blades from the opening in the patient's chest.

* * * * *